US009795329B2

United States Patent
Gerlitz

(10) Patent No.: US 9,795,329 B2
(45) Date of Patent: Oct. 24, 2017

(54) NON-INVASIVE DEVICE AND METHOD FOR MEASURING A SUBSTANCE CONCENTRATION

(71) Applicant: GlucoVista, Inc., Fairfield, NJ (US)

(72) Inventor: Yonatan Gerlitz, Herzliya (IL)

(73) Assignee: GlucoVista Inc., Fairfield, NJ (US)

( * ) Notice: Subject to any disclaimer, the term of this patent is extended or adjusted under 35 U.S.C. 154(b) by 0 days.

(21) Appl. No.: 14/595,105

(22) Filed: Jan. 12, 2015

(65) Prior Publication Data
US 2015/0196233 A1 Jul. 16, 2015

Related U.S. Application Data

(60) Provisional application No. 61/925,849, filed on Jan. 10, 2014.

(51) Int. Cl.
| | |
|---|---|
| A61B 5/1455 | (2006.01) |
| A61B 5/00 | (2006.01) |
| A61B 5/01 | (2006.01) |
| A61B 5/145 | (2006.01) |
| G01N 21/359 | (2014.01) |
| G01N 21/49 | (2006.01) |

(52) U.S. Cl.
CPC .......... *A61B 5/1455* (2013.01); *A61B 5/0059* (2013.01); *A61B 5/01* (2013.01); *A61B 5/14532* (2013.01); *A61B 5/6816* (2013.01); *A61B 5/7203* (2013.01); *A61B 5/7246* (2013.01); *A61B 5/0075* (2013.01); *A61B 2562/0238* (2013.01); *G01N 21/359* (2013.01); *G01N 21/49* (2013.01)

(58) Field of Classification Search
CPC ....... A61B 5/1455; A61B 5/0059; A61B 5/01; A61B 5/14532; A61B 5/6816; A61B 5/7203; A61B 5/7246; A61B 5/0075; A61B 2562/0238; G01N 21/359; G01N 21/49
USPC .......................................................... 600/301
See application file for complete search history.

(56) References Cited

U.S. PATENT DOCUMENTS

| | | | |
|---|---|---|---|
| 5,676,143 A | 10/1997 | Simonsen et al. | |
| 5,737,078 A | 4/1998 | Takarada et al. | |
| 2004/0167382 A1* | 8/2004 | Gardner ............... | A61B 5/0059 600/310 |
| 2004/0191119 A1* | 9/2004 | Zanzucchi ............. | A61B 5/151 422/504 |

(Continued)

FOREIGN PATENT DOCUMENTS

| | | |
|---|---|---|
| EP | 377249 | 4/1987 |
| WO | WO2010033104 | 3/2010 |

OTHER PUBLICATIONS

International Searching Authority; International Search Report and Written Opinion for Application No. PCT/US2015/011062 dated Apr. 2, 2015, Apr. 2, 2015.

Primary Examiner — Carl H Layno
Assistant Examiner — Erin M Piateski
(74) Attorney, Agent, or Firm — Parsons Behle & Latimer

(57) ABSTRACT

A system includes a light source and a light detector. The system further includes a first optical system configured to direct a transmitted portion of light onto the detector. The first optical system is further configured to block a scattered portion of the light. The system also includes a second optical system configured to direct the transmitted and scattered portions of the light onto the detector.

22 Claims, 4 Drawing Sheets

(56) References Cited

U.S. PATENT DOCUMENTS

| | | | |
|---|---|---|---|
| 2007/0197886 A1* | 8/2007 | Naganuma | A61B 5/0095 600/322 |
| 2007/0201028 A1 | 8/2007 | Myers et al. | |
| 2007/0203405 A1* | 8/2007 | Shimomura | A61B 5/14532 600/316 |
| 2007/0255141 A1* | 11/2007 | Esenaliev | A61B 5/1075 600/475 |
| 2009/0043178 A1* | 2/2009 | Belotserkovsky | A61B 5/14532 600/310 |
| 2009/0259407 A1* | 10/2009 | Gerlitz | A61B 5/14532 702/19 |
| 2013/0237797 A1* | 9/2013 | Muller | A61B 5/14532 600/407 |

* cited by examiner

NON-INVASIVE DEVICE AND METHOD FOR MEASURING A SUBSTANCE CONCENTRATION

CROSS REFERENCE TO RELATED APPLICATIONS

This disclosure claims the benefit of U.S. Provisional Patent Application No. 61/925,849 filed on Jan. 10, 2014 and entitled "Non-invasive Device and Method for Measuring a Substance Concentration in the Blood," the contents of which are hereby incorporated by reference in their entirety.

BACKGROUND

Determining an amount or a concentration of glucose within a body may be valuable for many purposes. Some benefits of determining a concentration of glucose within a body include health benefits, such as diagnosing and treating health issues, research benefits, health monitoring benefits, and many more benefits. Unfortunately, determining a concentration of glucose in a body may include invasive testing that may be painful or harmful to a subject.

Systems for non-invasively measuring a concentration of glucose are under development. Such systems often rely on a correlation between an amount of light absorbed or transmitted through the body and the concentration of glucose. However many factors and lurking variables may affect the amount of light absorbed or transmitted. Known systems for non-invasively measuring a concentration of glucose in a body may be less accurate because they do not take into account parameters in addition to the amount of light absorbed or transmitted through the body that may also correlate to the concentration of glucose.

SUMMARY

Disclosed is a non-invasive system and method for measuring a substance concentration that mitigates one or more of the above mentioned shortcomings of the known systems. In an embodiment, a system includes a light source and a light detector. The system further includes a first optical system configured to direct a transmitted portion of light onto the detector and further configured to block a scattered portion of the light. The system also includes a second optical system configured to direct the transmitted and scattered portions of the light onto the detector.

In an embodiment, a method includes measuring transmitted light from a body for at least one wavelength band via a first optical system. The method further includes measuring scattered light from the body for the at least one wavelength band via a second optical system. The method also includes determining a substance concentration in the body based on a predetermined correlation between measurement data and the substance concentration. The measurement data is associated with the measured transmitted light and the measured scattered light.

In an embodiment, a non-transitory computer-readable medium stores instructions that, when executed by a processor, cause the processor to initiate or perform operations. The operations include receiving a measurement of transmitted light from a body for at least one wavelength band via a first optical system. The operations further include receiving a measurement of scattered light from the body for the at least one wavelength band via a second optical system. The operations also include determining a substance concentration in the body based on a predetermined correlation between measurement data and a glucose concentration. The measurement data is associated with the measurement of transmitted light and the measurement of scattered light.

The features, functions, and advantages that have been discussed can be achieved independently in various embodiments or may be combined in yet other embodiments further details of which can be seen with reference to the following description and drawings.

BRIEF DESCRIPTION OF THE DRAWINGS

Some embodiments are described below with reference to the following accompanying drawings.

DETAILED DESCRIPTION

Figure 1A:
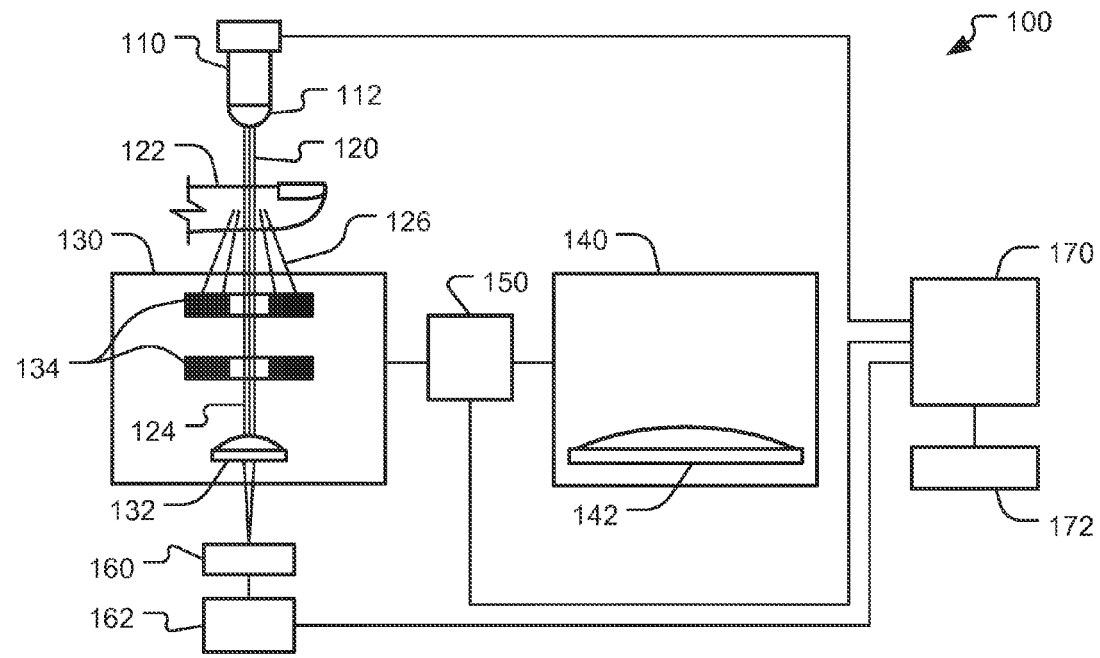
FIG. 1A depicts an embodiment of a system for determining a substance concentration in a first configuration.

It will be understood that the details of features described with respect to individual embodiments may be used in like features of the other embodiments described herein as consistent and appropriate even though not expressly indicated in describing the other embodiments.

Non-invasive measurement of a concentration of a substance, such as glucose, within a body may be performed using principles associated with small-angle scattering. For example, an amount of light found within the range of small-angle scattering after passing through a body may depend on an amount of scattering caused by the body and on an amount of scattering caused by the substance within the body. The amount of scattering caused by the substance may be dependent on a concentration of the substance within the body.

To illustrate, a collimated light beam may pass through a body, or a portion of a body. A portion of the collimated light beam may pass through the body without being scattered, resulting in transmitted (e.g., parallel) light. Another portion of the collimated light beam may be scattered within a range of small-angle scattering resulting in scattered light. An example of a range of small-angle scattering is from greater than 0° to 10° relative to transmitted or parallel light. Another portion of the collimated light beam may be scattered at angles outside the range of small-angle scattering (e.g., at angles greater than 10°). As used herein, transmitted light includes light that is not absorbed, scattered, or reflected.

Observation indicates that glucose in a solution reduces the angles of small-angle light scattering otherwise exhibited in the absence of glucose. A higher concentration of some substances, such as glucose, within the body may reduce scattering angles of light received by the body, thereby increasing the amount of radiation found within the range of small-angle scattering. For example, the portion of the collimated light beam scattered at angles outside the range of small-angle scattering may be reduced when concentrations of glucose increase. As such, a correlation may exist between an amount of radiation within the range of small-angle scattering and the concentration of glucose within the body. Another correlation may exist between an amount of transmitted radiation and the concentration of glucose within the body. Hence, a glucose concentration within the body may be determined by mapping a combination of scattered radiation and transmitted radiation to the glucose concentration.

The correlation between an amount of radiation within the range of small-angle scattering and the concentration of a substance within the body may also depend on other parameters. For example, an accurate determination of the substance concentration may further take into consideration an amount of transmitted light, ambient temperature, body surface temperature at the point of measurement, and body temperature measured at a location of the body that is consistent throughout each measurement of light.

Referring to FIG. 1A, an embodiment of a system 100 for determining a substance concentration is depicted in a first configuration. The system 100 may include a light source 110, a first optical system 130, a second optical system 140, and a detector 160.

The light source 110 may include an infrared (IR), such as a near-infrared (NIR), laser diode to generate IR light, such as NIR light in the range of 750 nm to 6,000 nm. Further, in some embodiments, the light source 110 may be configured to selectively generate light in a first wavelength band and a second wavelength band. The first wavelength band may include wavelengths, particularly in the IR region or NIR region, where a substance, such as glucose, has an effect on absorption of transmitted light. For example, the first wavelength band may be within the range of about 1130 nm to about 1190 nm (e.g., a 1160 nm operating wavelength) or within the range of 1300 nm to 1500 nm (e.g., a 1460 nm operating wavelength). The second wavelength band may include wavelengths where the substance has no effect or negligible effect on absorption of transmitted light. For example, the second wavelength band may be within the range of about 800 nm to about 905 nm (e.g., a 870 nm or a 880 nm operating wavelength), or may be within a range that includes a 960 nm or a 1120 nm operating wavelength. Beneficially, the first wavelength may be 1160 nm and the second wavelength may be 960 nm. Some embodiments may include two light sources, as described with reference to FIGS. 2A-2B.

The light source 110 may include or be coupled to a collimating lens 112. The collimating lens 112 may receive a diverging light beam emitted from the light source 110 and collimate the diverging light beam to form a collimated light beam 120. The function of the collimating lens 112 may be accomplished by multiple lenses. As explained above, the collimated light beam 120 may selectively include light within a first wavelength band, where the substance to be measured affects glucose absorption of the light, or a second wavelength band, where the substance has no effect or negligible effect on absorption of the light.

In the first configuration depicted in FIG. 1A, the light source 110 and the first optical system 130 may be configured to receive a body 122, or a portion of the body 122, therebetween. For example, as depicted in FIG. 1A, the portion of the body 122 may include a finger. In other embodiments, a different portion of a body may be received. The body 122 may scatter a portion of the collimated light beam 120 as the collimated light beam 120 passes through the body 122, thereby producing transmitted light 124 and scattered light 126. The scattered light 126 may include light that is scattered within the range of small-angle scattering.

The first optical system 130 may include a lens 132. An effective aperture diameter of the lens 132 may be selected such that the lens 132 captures the transmitted light 124, while at least a portion of the scattered light 126 is not captured by the lens 132. The exact diameter of the effective aperture of the lens 132 may depend on a distance between the lens 132 and the light source 110. The lens 132 may also be focused to infinity in order to capture the transmitted light 124 and direct the transmitted light 124 to the detector 160. To achieve this objective, the lens 132 may have an f-number of greater than or equal to f/3.

The first optical system 130 may further include one or more field limiters 134 to inhibit reception of the scattered light 126 at the lens 132. For example, the field limiters 134 may pass light within a range of angles including the transmitted light 124 and block light within a wider range of angles including the scattered light 126. Further, the field limiters 134 may be spaced within the first optical system 130 to limit an amount of reflected light and light from other sources otherwise received at the lens 132. As such, the first optical system 130 may direct the transmitted light 124 onto the detector 160 while blocking the scattered light 126. Although FIG. 1A depicts two field limiters 134, other embodiments may include more or fewer than two field limiters. In some embodiments, the field limiters 134 may be omitted altogether.

The second optical system 140 may include a lens 142, and may be selectively positioned between the light source 110 and the detector 160 interchangeably with the first optical system 130, as further described with reference to FIG. 1B. For example, the system 100 may include a motor 150 to selectively position the first optical system 130 or the second optical system 140 between the light source 110 and the detector 160. As such, the transmitted light 124 and the scattered light 126 may be selectively passed through either the first optical system 130 or the second optical system 140.

While in the first configuration depicted in FIG. 1A, the transmitted light 124 may be directed onto the detector 160. The detector 160 may be or include an IR detector or a NIR detector. In an embodiment, the detector 160 includes silicon, aluminum gallium arsenide, another material capable of detecting and measuring light, or combinations thereof.

Further, the detector 160 may be coupled to and function in unison with a lock-in amplifier 162. The lock-in amplifier 162 may filter, or otherwise adjust, a measurement of light detected by the detector 160 to remove or reduce data corresponding to noise, such as from external light and ambient radiation, based on a reference signal. As an example, the reference signal may correspond to light within the second wavelength band, where the substance has no effect or negligible effect on the absorption of light. In some embodiments, the lock-in amplifier 162 may be omitted.

The system 100 may further include a processor 170 and a memory 172. The processor may be coupled with and may send instructions to and receive instructions and/or data from the light source 110, the motor 150, and the detector 160. The memory 172 may include processor-readable instructions that, when executed by the processor 170, cause the processor 170 to perform operations as described herein. The processor 170 may include a microprocessor, such as a central processing unit (CPU), a digital signal processor (DSP), a peripheral interface controller (PIC), other processing circuitry or logic, or combinations thereof.

The memory 172 may include any device capable of storing processor-readable instructions including any type of memory device capable of storing processor-readable data, such as an optical disc (e.g., BLU-RAY DISC memory, digital video disc (DVD) memory, compact disc (CD) memory, etc.), a hard disk (e.g., magnetic disk memory, solid state memory, etc.), a read only memory (e.g., programmable read only memory (PROM), electrically erasable programmable read only memory (EEPROM), flash memory, etc.), a random access memory (e.g., dynamic random access memory (DRAM), magnetic random access memory (MRAM), etc.), another type of memory capable of storing computer readable data, or combinations thereof.

During operation of the system 100, in the first configuration, the light source 110, alone or in combination with the collimating lens 112, may generate the collimated light beam 120. The collimated light beam 120 may be transmitted through the body 122. As the collimated light beam 120 is transmitted through the body 122, a portion of it may be scattered to form scattered light 126 and transmitted light 124. The field limiters 134 may block the scattered light 126 and may pass the transmitted light 124, which may be received at the lens 124. The lens 132 may focus the transmitted light 124 onto the detector 160. In an embodiment, the lens 132 is small enough to prevent scattered light from being received at the lens 132. The detector 160 may measure the transmitted light 124 and the measurement may be transmitted as measurement data to the processor 170.

Figure 1B:
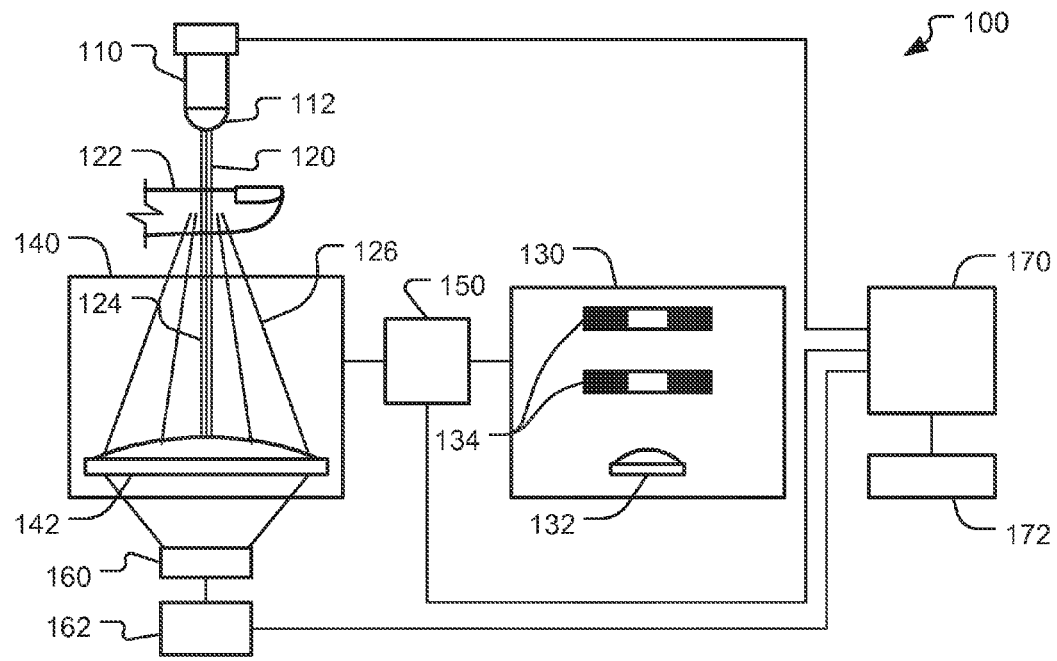
FIG. 1B depicts the FIG. 1A embodiment of the system for determining a substance concentration in a second configuration.

Referring to FIG. 1B, the embodiment of the system 100 for determining a substance concentration is depicted in a second configuration. The system 100 may be placed in the second configuration by activating the motor 150 to interchange the first optical system 130 with the second optical system 140. In the second configuration, the second optical system 140 may be aligned between the light source 110 and the detector 160. During operation of the system 100, in the second configuration, the scattered light 126 and the transmitted light 124 may be received at the lens 142 and directed onto the detector 160. The lens 142 may have an aperture diameter sufficiently large enough to capture light scattered within the range of small-angle scattering. For example, the effective aperture of the lens 142 may be large enough to receive light scattered by no more than 10° by the body 122. As such, it will be appreciated that the exact size of the effective aperture of the lens 142 may depend on a distance between the body 122 and the lens 142. Further, the lens 142 may include a lens with a F-number of f/1 or smaller. As such, the lens 142 may receive the transmitted light 124 and the scattered light 126 and direct the transmitted light 124 and the scattered light 126 onto the detector 160. The detector 160 may measure the combination of the transmitted light 124 and the scattered light 126 and the measurement may be transmitted as part of the measurement data to the processor 170.

The operations described herein with reference to FIGS. 1A-1B may be performed for a first wavelength band and for a second wavelength band. For example, while in the first configuration depicted in FIG. 1A, transmitted light may be measured at the detector 160 for a first wavelength band by emitting light that includes the first wavelength band from the light source 110. Transmitted light may be measured for a second wavelength band by emitting light that includes the second wavelength band from the light source 110. Similarly, while in the second configuration depicted in FIG. 1B, scattered light may be measured at the detector 160 for the first wavelength band and for the second wavelength band. The measurements may be transmitted to the processor 170 as measurement data.

To further illustrate, the light source 110 may switch between emitting light within the first wavelength band and light within the second wavelength band, thereby modulating the light source 110. The first wavelength band may correspond to wavelengths where the substance has an effect on light absorption during transmission. The second wavelength band may correspond to wavelengths where the substance has no effect or negligible effect on light absorption during transmission.

The processor 170 may determine a substance concentration in the body based on a predetermined correlation between the received measurement data and the substance concentration. As part of the determination both the measurements corresponding to the scattered light and the transmitted light may be normalized against their respective incident beams to produce a percentage of light transferred.

Further, during calibration (e.g., while defining the predetermined correlation) when looking at each level of glucose, measurements from both the first wavelength band and the second wavelength band may be used to estimate glucose. Measurements taken from the first wavelength band may show the change in glucose and measurements taken from the second wavelength band may be used as a reference point. Both wavelength bands may be used during measurement of the scattered light and the transmitted light and the changes in the first wavelength band (e.g., where glucose affects absorption of light) may be normalized against the reference wavelength band (e.g., where glucose has no effect or a negligible effect on the absorption of light).

One method of calculating glucose is to determine the correlation between the scattered light (within both the wavelength bands) and glucose and separately determine the correlation between transferred light (again within both wavelength bands). Then, a weighted average factor may be determined between the two correlations to achieve a glucose measurement across the entire glucose range. This factor may be a function rather than a signal constant.

As would be recognized by persons of ordinary skill in the art, the process described above for determining the predetermined correlation may also be used to determine a concentration of glucose within the body based on the predetermined correlation. For example, the weighted average of the two correlations may be mapped to a concentration of glucose within the body using the predetermined correlation.

In an embodiment, the measurement data may be modified or adjusted before being used to determine the substance concentration. For example, additional parameters may be taken into account and the measurement data may be adjusted based on the additional parameters. To illustrate, the processor 170 may receive a measurement of ambient temperature, a measurement of a body surface temperature, a measurement of a body temperature at a location of the body that is consistent throughout each measurement of light; or combinations thereof. Before determining the substance concentration, the processor 170 may modify the measurement data, the predetermined correlation, or both, based on the ambient temperature, the body surface temperature, the body temperature, or combinations thereof. Modification of measurement data may occur according to the teachings by the present inventor in U.S. Pat. No. 8,401,604 issued Mar. 19, 2013 and U.S. Pat. No. 8,611,975 issued Dec. 17, 2013, which are herein incorporated by reference.

A benefit associated with the system 100 is that an amount of light being scattered within the small-angle scattering range may be used to determine a concentration of a substance within a body as opposed to systems that do not include a first and second optical system. For example, based on a predetermined correlation of light within the small-angle scattering range, an amount of detected scattered light and transmitted light may be mapped to a corresponding concentration of the substance, thereby producing an accurate, or more accurate, determination of the concentration of the substance within the body. Other benefits of the system 100 may be apparent to persons of skill in the art having the benefit of this disclosure.

Figure 2A:
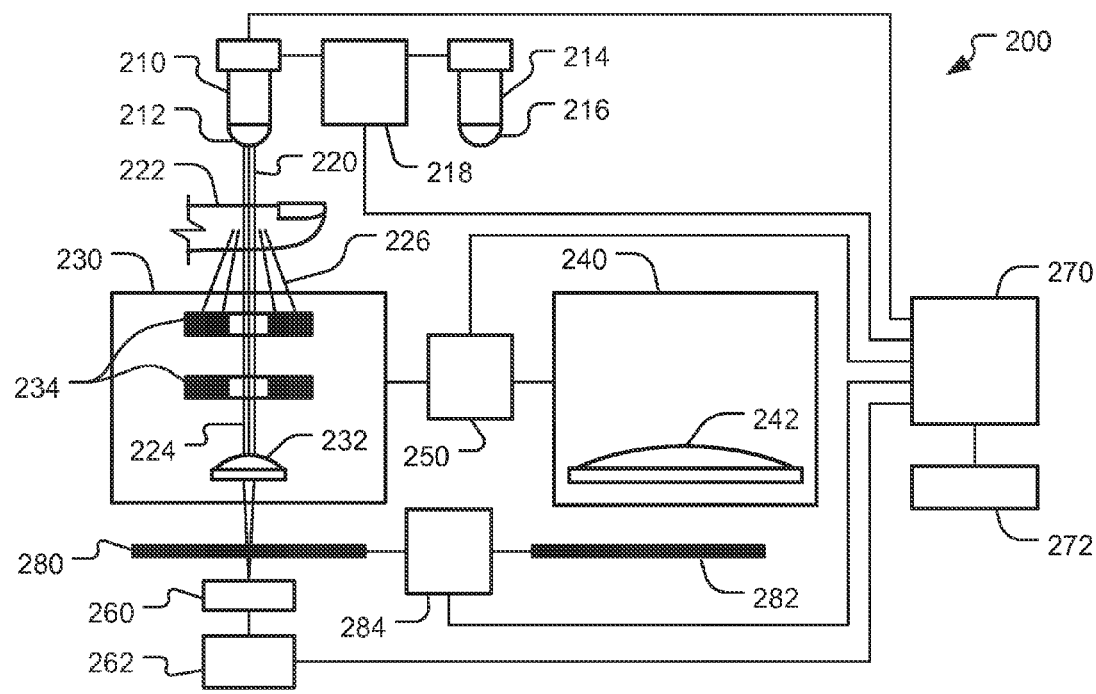
FIG. 2A depicts another embodiment of a system for determining a substance concentration in a first configuration.

Referring to FIG. 2A, a second embodiment of a system 200 for determining a substance concentration is depicted in a first configuration. The system 200 may include a first light source 210, a second light source 214, a first optical system 230, a second optical system 240, a first filter 280, a second filter 282, and a detector 160.

The first light source 210 may include an infrared (IR), such as a near-infrared (NIR), laser diode to generate IR, such as NIR, light within a first wavelength band. The first wavelength band may include wavelengths, particularly in the IR region or NIR region, where a substance, such as glucose, has an effect on absorption of light. Further, the first light source 210 may include or be coupled to a first collimating lens 212. The first light source 210, in combination with the collimating lens 212, may generate a collimated light beam 220 in the first wavelength band while in the first configuration.

The second light source 214 may include an infrared (IR) or a near-infrared (NIR) laser diode to generate IR or NIR light within a second wavelength band. The second wavelength band may include wavelengths where the substance has no effect or negligible effect on absorption of light. The second light source 214 may include or be coupled to a second collimating lens 216. In a second configuration, described further with reference to FIG. 2B, the second light source 214, in combination with the second collimating lens 216, may generate the collimated light beam 220 in the second wavelength band.

The system 200 may include a motor 218 to selectively position the first light source 210 or the second light source 214 in alignment with the detector 260. Although FIG. 2A depicts a first light source 210 and a second light source 114, in some embodiments, the system 200 may include a single light source configured to selectively generate light in the first wavelength band and the second wavelength band as described with reference to the light source 110 of FIGS. 1A-1B.

In the first configuration depicted in FIG. 2A, the light source 210 and the first optical system 230 may be configured to receive a body 222, or a portion of the body 222, therebetween. For example, as depicted in FIG. 2A, the portion of the body 222 may include a finger. In other embodiments, another portion of a body may be received. The body 222 may scatter a portion of the collimated light beam 220 as the collimated light beam 220 passes through the body 222, thereby producing transmitted light 224 and scattered light 226. The scattered light 226 may include light that is scattered within the range of small-angle scattering.

The first optical system 230 may include a lens 232. An effective aperture diameter of the lens 232 may be selected such that the lens 232 captures the transmitted light 224, while at least a portion of the scattered light 226 is not captured by the lens 232. The exact diameter of the effective aperture of the lens 232 may depend on a distance between the lens 232 and the light source 210 or the light source 214. The lens 232 may also be focused to infinity in order to capture the transmitted light 224 and direct the transmitted light 224 to the detector 260. To achieve this objective, the lens 232 may have an F-number of greater than or equal to f/3.

The first optical system 230 may further include one or more field limiters 234 to inhibit receipt of the scattered light 226 at the lens 232. For example, the field limiters 234 may pass light within a range of angles including the transmitted light 224 and block light within a wider range of angles including the scattered light 226. Further, the field limiters 234 may be spaced within the first optical system 230 to limit an amount of reflected light and light from other sources received at the lens 232. As such, the first optical system 230 may direct the transmitted light 224 onto the detector 260 while blocking the scattered light 226. Although FIG. 2A depicts two field limiters 234, other embodiments may include more or fewer than two field limiters. In some embodiments, the field limiters 234 may be omitted.

The second optical system 240 may include a lens 242, and may be selectively positioned between the light source 210 and the detector 260 interchangeably with the first optical system 230. For example, the system 200 may include a motor 250 to selectively position the first optical system 230 or the second optical system 240 between the light source 210 and the detector 260. As such, the transmitted light 224 and the scattered light 226 generated by the first light source 210 within the first wavelength band may be selectively passed through the first optical system 230 or the second optical system 240. The second optical system 240 is further described with reference to FIG. 2B.

The first filter 280 may include an interference filter configured to pass light within a first wavelength band. The first wavelength band may correspond to a wavelength band of light emitted by the first light source 210 and may include wavelengths in which a substance affects absorption of light by the body 222. Further, the first filter 280 may block light within a second wavelength band, where the substance has no or negligible effect on absorption of light by the body 222. By blocking light within the second wavelength, the first filter 280 may reduce interference at the detector 260 from light within the second wavelength band. Further, the first filter 280 may block ambient light, thereby also reducing interference from ambient light at the detector 260. The function of the first filter 280 may be accomplished by multiple filters.

The second filter 282 may also include an interference filter. For example, the second filter 282 may be configured to block light within the first wavelength band, corresponding to a wavelength band in which the substance affects absorption of light by the body 222. Further, the second filter 282 may pass light within the second wavelength band, where the substance has no or negligible effect on absorption of light by the body 222. By blocking light within the first wavelength, the second filter 282 may reduce interference at the detector 260 from light within the first wavelength band, as described further with reference to FIG. 2B. The second filter 282 may further block ambient light, thereby also reducing interference from ambient light at the detector 260. The function of the second filter 282 may be accomplished by multiple filters.

Figure 2B:
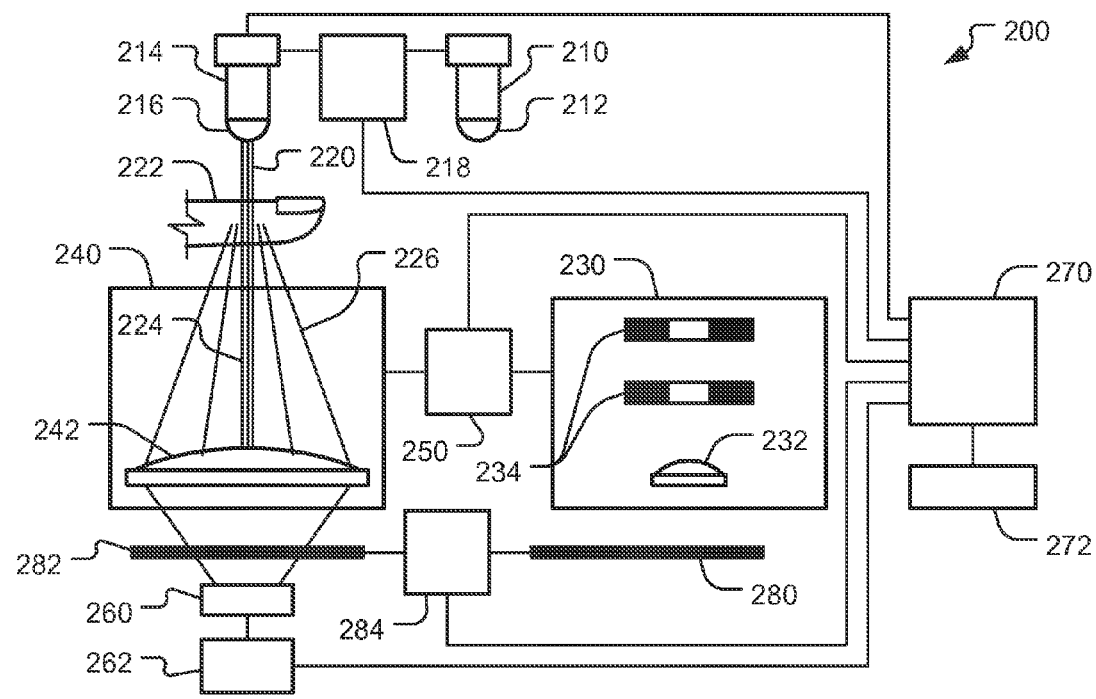
FIG. 2B depicts the FIG. 2A embodiment of the system for determining a substance concentration in a second configuration.

The system 200 may include a motor 284 to selectively position the first filter 280 or the second filter 282 between the light source 210 and the detector 260, as described herein. Although FIGS. 2A and 2B depict the system 200 as including two filters, in some embodiments, the system 200 may include a single filter 280. In these embodiments, the first wavelength band may include a wavelength band where glucose affects absorption of light and the second wavelength band may be an entire NIR spectrum emitted by the light source 210 or the light source 220. Measurements within the first wavelength band may be performed using the filter 280 and measurements within the second wavelength band may be performed while the filter 280 is removed, such as by the motor 284. Further, in some embodiments, both the first filter 280 and the second filter 282 may be omitted. In these embodiments, the first light source 210 and the second light source 214 may use single wavelength lasers to apply only those wavelengths that fall within the first wavelength band for the first light source 210 and within the second wavelength band for the second light source 214. As described herein, in some embodiments, a single light source may selectively apply wavelengths that fall within the first wavelength band and wavelengths that fall within the second wavelength band.

While in the first configuration, the transmitted light 224 may be directed onto the detector 260. The detector 260 may include an IR detector or a NIR detector. In an embodiment, the detector 260 includes silicon, aluminum gallium arsenide, another material capable of detecting and measuring light, or combinations thereof.

Further, the detector 260 may be coupled to and function in unison with a lock-in amplifier 262. The lock-in amplifier 262 may filter, or otherwise adjust, a measurement of light detected by the detector 260 to remove or reduce data corresponding to noise, such as from external light and ambient radiation, based on a reference signal. For example, the reference signal may correspond to light within the second wavelength band, where the substance has no effect or negligible effect on the absorption of light. In some embodiments, the lock-in amplifier 262 may be omitted.

The system 200 may further include a processor 270 and a memory 272. The processor 270 may be coupled with and may send instructions to and receive instructions or data from the first light source 210, the second light source 214, the motors 218, 250, 284, and the detector 260. The memory 272 may include processor readable instructions that, when executed by the processor, cause the processor to perform operations as described herein. The processor 270 may include a microprocessor, such as a central processing unit (CPU), a digital signal processor (DSP), a peripheral interface controller (PIC), another processing circuit or logic, or combinations thereof.

The memory 272 may include any device capable of storing processor-readable instructions including, such as an optical disc (e.g., BLU-RAY DISC memory, digital video disc (DVD) memory, compact disc (CD) memory, etc.), a hard disk (e.g., magnetic disk memory, solid state memory, etc.), a read only memory (e.g., programmable read only memory (PROM), electrically erasable programmable read only memory (EEPROM), flash memory, etc.), a random access memory (e.g., dynamic random access memory (DRAM), magnetic random access memory (MRAM), etc.), another type of memory capable of storing computer readable data, or combinations thereof.

Although FIGS. 2A and 2B depict two configurations, as will be recognized by those of skill in the art having the benefit of this disclosure, additional configurations are possible. For example, in the first configuration, the light source 210, the optical system 230, and the filter 280 are aligned with the body 222 and the detector 260, as depicted in FIG. 2A. In a second configuration, the light source 210, the optical system 230, and the filter 282 are aligned with the body 222 and the detector 260. In a third configuration, the light source 210, the optical system 240, and the filter 280 are aligned with the body 222 and the detector 260. In a fourth configuration, the light source 210, the optical system 240, and the filter 282 are aligned with the body 222 and the detector 260. In a fifth configuration, the light source 214, the optical system 230, and the filter 280 are aligned with the body 222 and the detector 260. In a sixth configuration, the light source 214, the optical system 230, and the filter 282 are aligned with the body 222 and the detector 260. In a seventh configuration, the light source 214, the optical system 240, and the filter 280 are aligned with the body 222 and the detector 260. In an eighth configuration, the light source 214, the optical system 240, and the filter 282 are aligned with the body 222 and the detector 260, as depicted in FIG. 2B.

During operation of the system 200, the light source 210, alone or in combination with the collimating lens 212, may generate the collimated light beam 220 within a first wavelength band. The first wavelength band may correspond to wavelengths in which a substance, such as glucose, has an effect on the absorption of light. The collimated light beam 220 may pass through the body 222. As the collimated light beam 220 passes through the body 222, a portion of it may be scattered to form scattered light 226 and transmitted light 224. The scattered light 226 and the transmitted light 224 may be received at the first optical system 230. The field limiters 234 may block the scattered light 226 and may pass the transmitted light 224. The transmitted light 224 may be received at the lens 232. The lens 232 may focus the transmitted light 224 onto the detector 260 through the interference filter 280. In an embodiment, the lens 232 is small enough to prevent scattered light from being received at the lens 232. The detector 260 may measure the transmitted light 224 within the first wavelength band and the measurement may be transmitted as data to the processor 270.

Further during operation of the system 200, the motor 218 may interchange the light sources 212, 214 (e.g., replacing the first light source 210 with the second light source 216 in alignment with the detector 260). The light source 214, alone or in combination with the collimating lens 216, may generate the collimated light beam 220 within a second wavelength band. The second wavelength band may correspond to wavelengths in which the substance has no effect or negligible effect on the absorption of light. The first optical system 230 may direct the transmitted light 224 within the second wavelength band onto the detector 260 through the second filter 282. The motor 284 may interchange the filters 280, 282 (e.g., replacing the first filter 280 with the second filter 282 in alignment with the detector 260). The detector 260 may measure the transmitted light 224 within the second wavelength band and the measurement may be transmitted as part of the data to the processor 270.

Referring to FIG. 2B, the embodiment of the system 200 for determining a substance concentration is depicted in a second configuration. The system 200 may be placed in the second configuration by activating the motor 250 to interchange the first optical system 130 with the second optical system 140. In the second configuration, the second optical system 240 may be aligned between the light source 214 and the detector 260. In this configuration, the light source 214 may generate the collimated light beam 220 within the second wavelength band. The scattered light 226 and the transmitted light 224 may be received at the lens 242 and directed onto the detector 260. An effective aperture of the lens 242 may be sufficiently large enough to capture light scattered within the range of small-angle scattering. For example, the effective aperture of the lens 242 may be large enough to receive light scattered by no more than 10° by the body 222. As such, it will be appreciated that the exact diameter of the effective aperture of the lens 242 may depend on a distance between the body 222 and the lens 242. The lens 242 may include a lens with a f-number of f/1 or smaller. As such, the lens may receive the transmitted light 224 and the scattered light 226 and direct the transmitted light 224 and the scattered light 226 onto the detector 260. The detector 260 may measure the scattered light 226 and the measurement may be transmitted as part of the data to the processor 270.

During operation of the system 200 in the configuration of FIG. 2B, the motor 218 may interchange the light sources 210, 214 (e.g., replacing the second light source 214 with the first light source 210 in alignment with the detector 260) and the motor 284 may interchange the filters 280, 282 (e.g., replacing the second filter 282 with the first filter 280 in alignment with the detector 260). The light source 210, alone or in combination with the collimating lens 212, may generate the collimated light beam 220 within the first wavelength band. The second optical system 240 may direct the transmitted light 224 and the scattered light 226 within the second wavelength band onto the detector 260 through the second filter 282. The detector 260 may measure the transmitted light 224 and the scattered light 226 within the second wavelength band and the measurement may be transmitted as part of the data to the processor 270.

The processor 270 may determine a substance concentration in the body based on a predetermined correlation between measurement data and the substance concentration as described herein. In some embodiments, the measurement data may be modified or adjusted. For example, additional parameters may be taken into account to determine the substance concentration. To illustrate, the processor 270 may further receive a measurement of ambient temperature, a measurement of a body surface temperature, a measurement of a body temperature at a location of the body that is consistent throughout each measurement of light, or combinations thereof. Before determining the substance concentration, the processor 170 may modify the measurement data, the predetermined correlation, or both, based on the ambient temperature, the body surface temperature, the body temperature, or combinations thereof.

A benefit associated with the system 200 is that an amount of light being scattered within the small-angle scattering range may be used to determine a concentration of a substance within a body as opposed to systems that do not include a first and second optical system. Further accuracy may be obtained by normalizing both the measured scattered light and the measured transmitted light. For example, normalizing the measured scattered light may include calculating a scattered light ratio parameter based on a ratio of the measured scattered light for the first wavelength band to the measured scattered light for the second wavelength band and normalizing the measured transmitted light may include calculating a transmitted light ratio parameter based on a ratio of the measured transmitted light for the first wavelength band to the measured transmitted light for the second wavelength band. Hence, the system 200 may be more accurate than systems that do not include the second light source 214 and the filters 280, 282. Other benefits of the system 200 may be apparent to those of skill in the art having the benefit of this disclosure.

Figure 3:
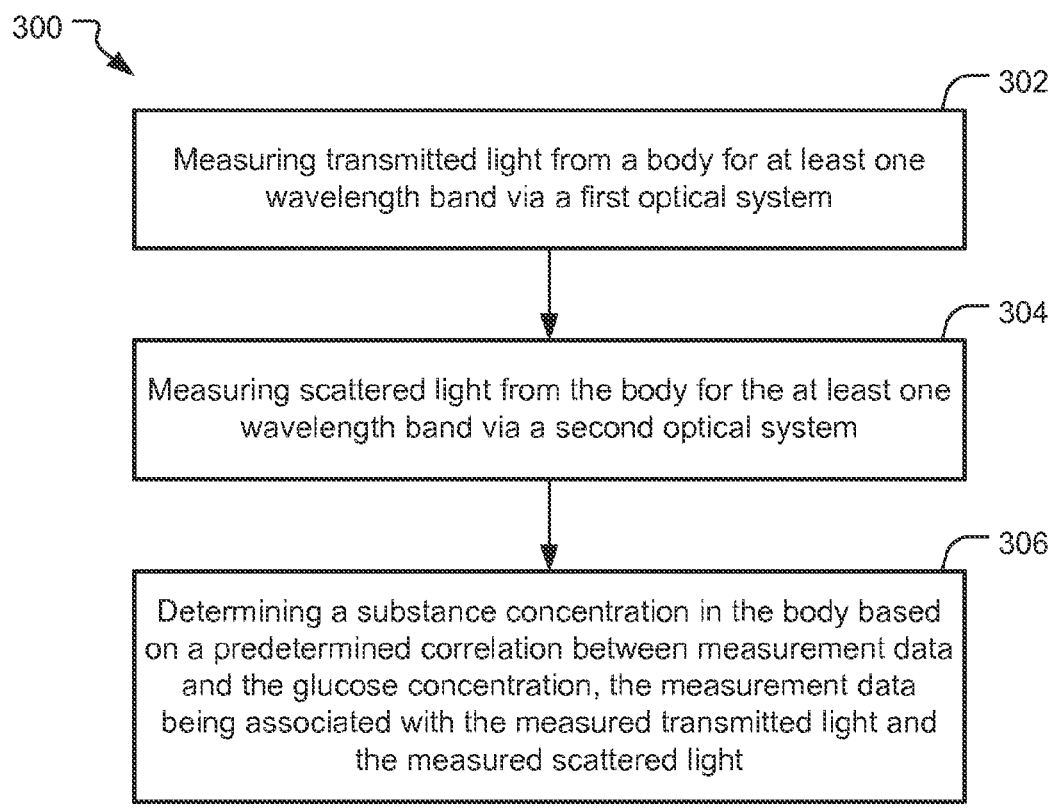
FIG. 3 depicts an embodiment of a method for determining a substance concentration.

Referring to FIG. 3, an embodiment of a method for determining a substance concentration is depicted and generally designated 300. The method 300 may include measuring transmitted light from a body for at least one wavelength band via a first optical system, at 302. For example, the light source 110 may generate a collimated light beam 120 in at least one wavelength band. The collimated light beam may be passed through the body 122 resulting in the transmitted light 124 and the scattered light 126. The first optical system 130 may direct the transmitted light 124 onto the detector 160 and may block the scattered light 126. The detector 160 may measure the transmitted light 124.

The method 300 may further include measuring transmitted light and scattered light passing through the body for the at least one wavelength band via a second optical system, at 304. For example, the second optical system 140 may direct the transmitted light 124 and the scattered light 126 onto the detector 160. The detector 160 may measure the transmitted light 124 and the scattered light 126.

The method 300 may also include determining a substance concentration in the body based on a predetermined correlation between measurement data and the glucose concentration, the measurement data being associated with the measured transmitted light and the measured scattered light, at 306. For example, the detector 160 may send measurement data corresponding to the measured transmitted light 124 and the measured transmitted light 124 and scattered light 126 to the processor 170. The processor 170 may determine a substance concentration in the body 122 based on a predetermined correlation between the measurement data and the glucose concentration.

A benefit of the method 300 is that a glucose level within the body may be non-invasively determined or more accurately determined as compared to methods that do not generate a measurement of transmitted light and a measurement of transmitted light and scattered light. The measurement of the transmitted and scattered light may include light scattered within the range of small-angle scattering. Other benefits of the method 300 may be apparent to those of skill in the art having the benefit of this disclosure.

Figure 4:
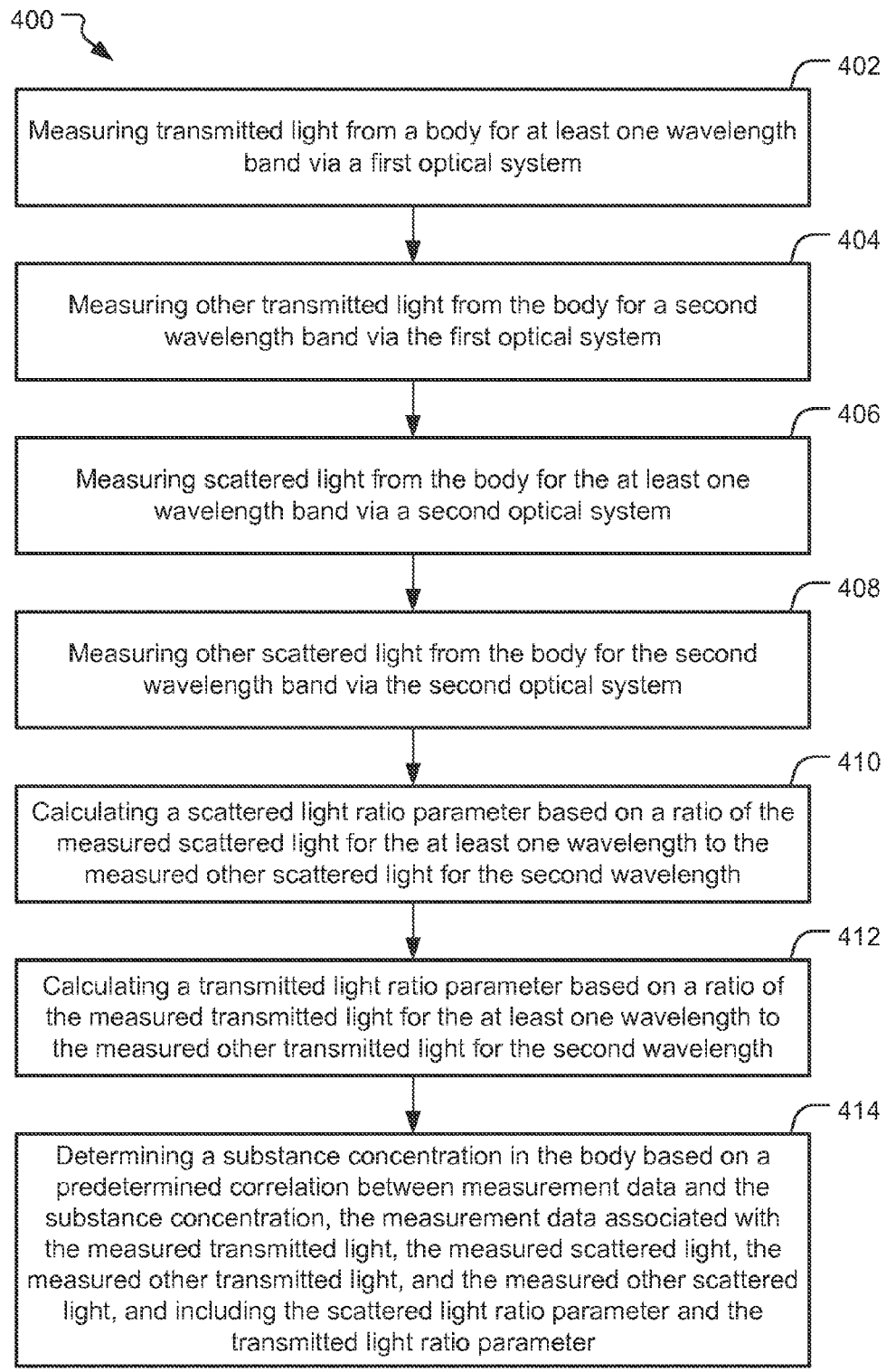
FIG. 4 depicts an embodiment of a method for determining a substance concentration.

Referring to FIG. 4, an embodiment of a method for determining a substance concentration is depicted and generally designated 400. The method 400 may include measuring transmitted light from a body for at least one wavelength band via a first optical system, at 402. For example, the light source 210 may generate a collimated light beam 220 in at least one wavelength band. The collimated light beam may be passed through the body 222 resulting in the transmitted light 224 and the scattered light 226. The first optical system 230 may direct the transmitted light 224 onto the detector 260 and may block the scattered light 226. The detector 260 may measure the transmitted light 224.

The method 400 may further include measuring other transmitted light from the body for a second wavelength band via the first optical system, at 404. For example, the light source 210 may be interchanged with the light source 216. The light source 216 may generate other light as the collimated light beam 220 in a second wavelength band. Alternatively, the light source 210 may generate a collimated light beam 220 in a second wavelength band. The collimated light beam 220 may pass through the body 222 resulting in the transmitted light 224 and the scattered light 226. The first optical system 230 may direct the transmitted light 224 onto the detector 260 and may block the scattered light 226. The detector 260 may measure the transmitted light 224 for the second wavelength band.

The method 400 may also include measuring scattered light from the body for the at least one wavelength band via a second optical system, at 406. For example, the light source 210 may generate a collimated light beam 220 in at least one wavelength band. The collimated light beam may pass through the body 222 resulting in the transmitted light 224 and the scattered light 226. The second optical system 240 may direct the transmitted light 224 and the scattered light 226 onto the detector 260. The detector 260 may measure the transmitted light 224 and the scattered light 226 in the at least one wavelength.

The method 400 may include measuring other scattered light from the body for the second wavelength band via the second optical system, at 408. For example, the light source 210 may be interchanged with the light source 216. The light source 216 may generate other light as the collimated light beam 220 in a second wavelength band. Instead, the light source 210 may generate a collimated light beam 220 in a second wavelength band. The collimated light beam may pass through the body 222 resulting in the transmitted light 224 and the scattered light 226. The second optical system 240 may direct the transmitted light 124 and the scattered light 226 onto the detector 260. The detector 260 may measure the transmitted light 224 and the scattered light 226 in the second wavelength. It will be appreciated 402, 404, 406, and 408 shown in FIG. 4 may be completed in a different order.

The method 400 may further include calculating a scattered light ratio parameter based on a ratio of the measured scattered light for the at least one wavelength to the measured other scattered light for the second wavelength, at 410. For example, the measured scattered light for the at least one wavelength and the measured scattered light for the second wavelength may be sent to the processor 270 as measurement data. The processor 270 may calculate a scattered light ratio based on the measurements.

The method 400 may also include calculating a transmitted light ratio parameter based on a ratio of the measured transmitted light for the at least one wavelength to the measured other transmitted light for the second wavelength, at 412. For example, the measured transmitted light for the at least one wavelength and the measured transmitted light for the second wavelength may be sent to the processor 270 as measurement data. The processor 270 may calculate a transmitted light ratio based on the measurements.

The method 400 may include determining a substance concentration in the body based on a predetermined correlation between measurement data and the substance concentration, the measurement data being associated with the measured transmitted light, the measured scattered light, the measured other transmitted light, and the measured other scattered light, and including the scattered light ratio parameter and the transmitted light ratio parameter, at 414. For example, the processor 270 may determine a substance concentration in the body 222 based on the scattered light ratio parameter and the transmitted light ratio parameter calculated at 410 and 412.

One or more of the methods described herein, such as the methods 300 and 400 may be performed or initiated by a processor, such as the processors 170 and 270, in response to instructions stored at a non-transitory computer readable medium, such as the memories 172 and 272. The non-transitory computer readable medium may include any type of memory device capable of storing computer readable data, such as an optical disc (e.g., BLU-RAY DISC memory, digital video disc (DVD) memory, compact disc (CD) memory, etc.), a hard disk (e.g., magnetic disk memory, solid state memory, etc.), a read only memory (e.g., programmable read only memory (PROM), electrically erasable programmable read only memory (EEPROM), flash memory, etc.), a random access memory (e.g., dynamic random access memory (DRAM), magnetic random access memory (MRAM), etc.), another type of memory capable of storing computer readable data, or combinations thereof.

In compliance with the statute, the embodiments have been described in language more or less specific as to structural and methodical features. It is to be understood, however, that the embodiments are not limited to the specific features shown and described. The embodiments are, therefore, claimed in any of their forms or modifications within the proper scope of the appended claims appropriately interpreted in accordance with the doctrine of equivalents.

TABLE OF REFERENCE NUMERALS FOR FIGURES

100 System
110 Light Source
112 Collimating Lens
120 Collimated Beam
122 Body
124 Transmitted Light
126 Scattered Light
130 Optical System
132 Lens
140 Optical System
142 Lens
144 Field Limiters
150 Motor
160 Detector
162 Lock-in Amplifier
170 Processor
172 Memory
200 System
210 Light Source
212 Lens
214 Light Source
216 Lens
218 Motor
220 Collimated Beam
222 Body
224 Transmitted Light
226 Scattered Light
230 Optical System
232 Lens
240 Optical System
242 Lens
244 Field Limiters
250 Motor
260 Detector
262 Lock-in Amplifier
270 Processor
272 Memory
280 Filter
282 Filter
284 Motor

What is claimed is:

1. A method comprising:
   providing a light source and directing light through a body that both transmits and scatters the light;
   via a first optical system, directing the transmitted light onto a light detector, the first optical system blocking the scattered light from the body with one or more field limiters such that the blocked light does not reach the light detector;
   measuring the transmitted light from the body in a wavelength band via the first optical system;
   via a second optical system, directing the transmitted light and a portion of the scattered light onto the light detector;
   measuring the portion of the scattered light from the body in the wavelength band via the second optical system; and
   determining a substance concentration in the body based on a predetermined correlation between measurement data and the substance concentration, the measurement data being associated with the measured transmitted light and the measured scattered light.

2. The method of claim 1, further comprising:
measuring the transmitted light from the body in another wavelength band via the first optical system;
measuring the portion of the scattered light from the body in the other wavelength band via the second optical system, the measurement data being further associated with the measured scattered light and the measured transmitted light in the other wavelength band.

3. The method of claim 2, the wavelength band including wavelengths where the substance has an effect on absorption of transmitted light and the other wavelength band including only wavelengths where the substance has no effect or negligible effect on absorption of transmitted light.

4. The method of claim 3, the light source including a near-infrared (NIR) laser diode and a collimating lens generating a collimated NIR light beam in the wavelength band when selected and in the other wavelength band when selected.

5. The method of claim 3, the light source including a first NIR laser diode and a first collimating lens generating a collimated NIR light beam in the wavelength band and including a second NIR laser diode and a second collimating lens generating a collimated NIR light beam in the other wavelength band.

6. The method of claim 3, further comprising an interference filter passing light within the wavelength band and blocking light within the other wavelength band.

7. The method of claim 6, further comprising a motor selectively positioning the interference filter between the light source and the light detector.

8. The method of claim 2, further comprising:
calculating a scattered light ratio parameter based on a ratio of the measured scattered light in the wavelength band to the measured scattered light in the other wavelength band;
calculating a transmitted light ratio parameter based on a ratio of the measured transmitted light in the wavelength band to the measured transmitted light in the other wavelength band, the measurement data including the scattered light ratio parameter and the transmitted light ratio parameter.

9. The method of claim 1, further comprising:
measuring an ambient temperature;
measuring a body surface temperature;
measuring a body temperature; and
before determining the substance concentration, modifying the measurement data, the predetermined correlation, or both, based on the ambient temperature, the body surface temperature, and the body temperature.

10. The method of claim 1, further comprising modulating the light source.

11. The method of claim 1, wherein the substance is glucose.

12. The method of claim 1, the first optical system including a lens with a f-number of f/3 or greater directing the transmitted light onto the light detector.

13. The method of claim 12, the one or more field limiters comprising two or more field limiters inhibiting receipt of the scattered light at the lens that would otherwise reach the light detector.

14. The method of claim 1, the second optical system including a lens with a f-number of f/1 or smaller directing the transmitted light and the portion of the scattered light onto the light detector.

15. The method of claim 1, the portion of the scattered light being limited to light scattered by the body within a range of small-angle scattering.

16. The method of claim 1, further comprising a motor selectively positioning the first optical system or the second optical system between the light source and the light detector.

17. The method of claim 1, the light detector comprising at least one material selected from silicon, aluminum gallium arsenide, and combinations thereof.

18. The method of claim 1, the light detector being coupled to a lock-in amplifier reducing detection of light noise from other light sources.

19. A method comprising:
providing a light source and directing light through a body that both transmits and scatters the light, the light being NIR light, the scattering including small-angle scattering in a range from greater than 0° to 10° relative to the transmitted light;
positioning a first optical system between the light source and a light detector and, via the first optical system, directing the transmitted light onto the light detector, the first optical system capturing the transmitted light with a lens having an effective aperture diameter selected such that at least a portion of the small-angle scattered light is not captured by the lens and does not reach the detector;
measuring the transmitted light from the body in a wavelength band via the first optical system;
measuring the transmitted light from the body in another wavelength band via the first optical system;
positioning a second optical system different from the first optical system between the light source and the light detector and, via the second optical system, directing the transmitted light and the small-angle scattered light onto the light detector;
measuring the small-angle scattered light from the body in the wavelength band via the second optical system;
measuring the small-angle scattered light from the body in the other wavelength band via the second optical system;
determining a substance concentration in the body based on a predetermined correlation between measurement data and the substance concentration, the measurement data being associated with the measured transmitted light and the measured scattered light in the wavelength band and being further associated with the measured transmitted light and the measured scattered light in the other wavelength band.

20. The method of claim 19, further comprising the first optical system blocking the scattered light from the body such that the blocked light does not reach the light detector.

21. The method of claim 20, the blocking of the scattered light occurring with one or more field limiters.

22. A method comprising:
providing a light source having a collimating lens and directing collimated light through a body that both transmits and scatters the collimated light, the collimated light being NIR light and the scattering including a range of small-angle scattering from greater than 0° to 10°;
via a first optical system, directing the transmitted light onto a light detector, the first optical system blocking the scattered light from the body with one or more field limiters such that the blocked light does not reach the light detector, capturing the transmitted light with a first lens, and directing the transmitted light onto the light detector, the first lens having an effective aperture diameter and a f-number greater than or equal to f/3 that are selected such that at least a portion of the small-angle scattered light cannot be captured by the first lens and reach the detector;

measuring the collimated, transmitted light from the body in a wavelength band via the first optical system;

measuring the collimated, transmitted light from the body in another wavelength band via the first optical system;

via a second optical system, capturing the transmitted light and the small-angle scattered light with a second lens and directing the transmitted light and the small-angle scattered light onto the light detector, the second lens having an effective aperture diameter and a f-number of f/1 or smaller that are selected such that all of the small-angle scattered light is captured by the second lens and reaches the detector;

measuring the small-angle scattered light from the body in the wavelength band via the second optical system;

measuring the small-angle scattered light from the body in the other wavelength band via the second optical system;

calculating a transmitted light ratio parameter based on a ratio of the measured transmitted light in the wavelength band to the measured transmitted light in the other wavelength band;

calculating a scattered light ratio parameter based on a ratio of the measured scattered light in the wavelength band to the measured scattered light in the other wavelength band;

determining a substance concentration in the body based on a predetermined correlation between measurement data and the substance concentration, the measurement data including the transmitted light ratio parameter and the scattered light ratio parameter.

* * * * *